United States Patent [19]

Ilavsky et al.

[11] 4,009,269
[45] Feb. 22, 1977

[54] ANTIBIOTIC COMPOSITIONS AND METHODS FROM *MICROMONOSPORA PURPUREA* JI-20

[75] Inventors: Jan Ilavsky, Livingston; Aris P. Bayan, New Brunswick; William Charney, Montclair; Hans Reimann, Wayne, all of N.J.

[73] Assignee: Schering Corporation, Kenilworth, N.J.

[22] Filed: June 9, 1975

[21] Appl. No.: 584,791

Related U.S. Application Data

[60] Division of Ser. No. 414,492, Nov. 9, 1973, Pat. No. 3,903,072, which is a continuation-in-part of Ser. No. 261,753, June 12, 1972, abandoned.

[52] U.S. Cl. .............................. 424/181; 424/114; 424/180
[51] Int. Cl.$^2$ ...................................... A61K 31/71
[58] Field of Search ............................ 424/114, 181

[56] References Cited

UNITED STATES PATENTS

| | | | |
|---|---|---|---|
| 3,651,042 | 3/1972 | Marquez et al. | 260/210 AB |
| 3,661,892 | 5/1972 | Shomura et al. | 260/210 R |

*Primary Examiner*—V. D. Turner
*Attorney, Agent, or Firm*—Carver C. Joyner; Stephen B. Coan; Raymond McDonald

[57] ABSTRACT

A mutant strain of *Micromonospora purpurea* herein designated *M. purpurea* JI-20 elaborates an antibiotic complex comprising gentamicin and at least two novel antibiotic substances namely Antibiotic JI-20A and Antibiotic JI-20B. The so-produced antibiotics have an adverse effect upon the growth of gram-positive and gram-negative bacteria.

6 Claims, 4 Drawing Figures

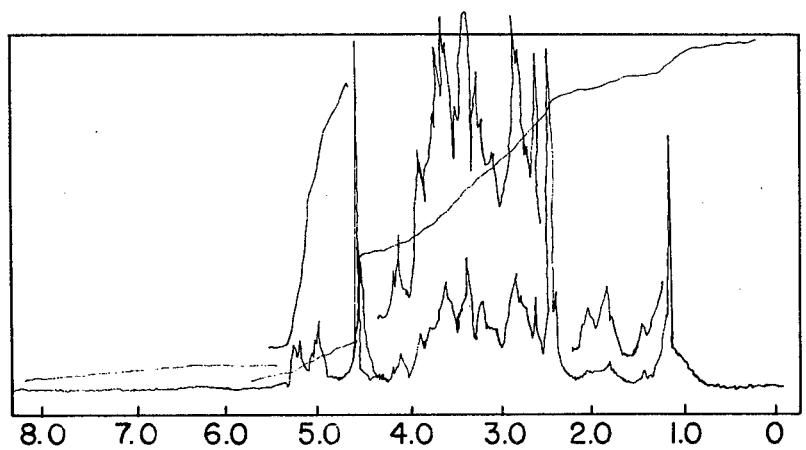
FIG. 1 ANTIBIOTIC JI-20A
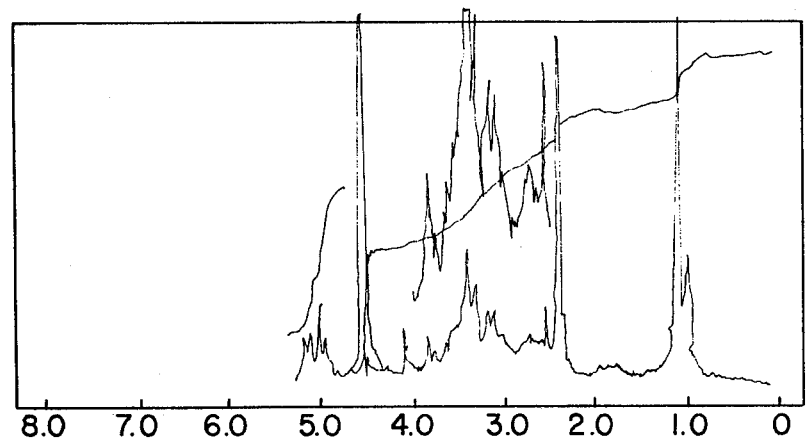
FIG. 2 ANTIBIOTIC JI-20B
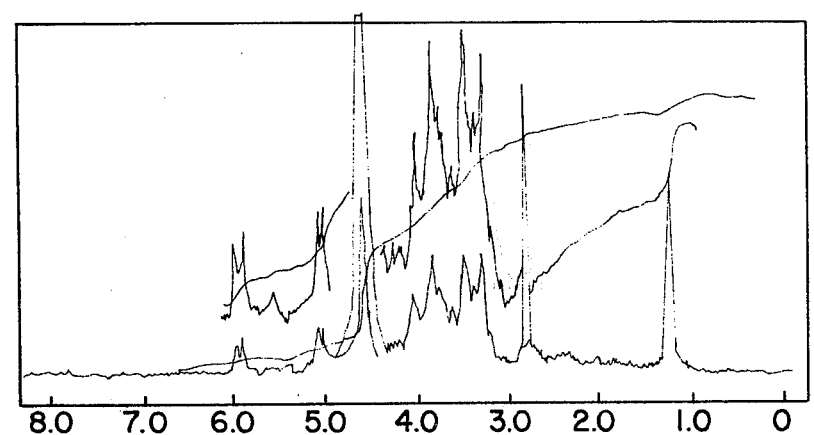
FIG. 3 ANTIBIOTIC JI-20A SULFATE SALT
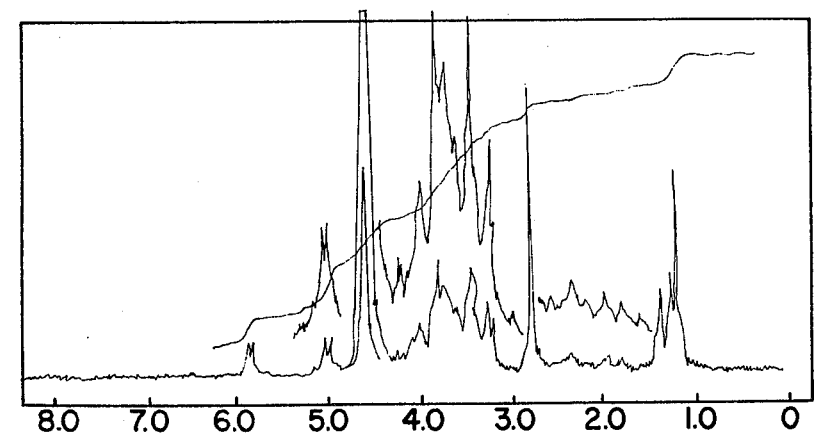
FIG. 4 ANTIBIOTIC JI-20B SULFATE SALT

ANTIBIOTIC COMPOSITIONS AND METHODS FROM *MICROMONOSPORA PURPUREA* JI-20

This application is a divisional of our copending application Ser. No. 414,492, filed Nov. 9, 1973, now U.S. Pat. No. 3,903,072, issued Sept. 2, 1975, which in turn is a continuation-in-part of application Ser. No. 261,753, filed June 12, 1972 (now abandoned).

BACKGROUND OF THE INVENTION

The importance of antibiotics in the treatment of animal and plant infections, and as growth factors is well known. The present invention provides a new antibiotic complex, the antibiotics being produced by an Actinomycete from the genus Micromonospora. The new antibiotic complex is herein designated Antibiotic JI-20 and the chemical, physical and biological properties set forth herein distinguish the components of the complex from all heretofore known antibiotics.

SUMMARY OF THE INVENTION

Cultivation of a mutant strain of *Micromonospora purpurea* NRRL 2953 (*Micromonospora purpurea* JI-20) in a suitable culture medium produces a composition having substantial antibiotic activity. The composition i.e. Antibiotic JI-20 complex consists of a very small quantity of gentamicin, plus a larger quantity of at least two novel components, namely Antibiotic JI-20A and Antibiotic JI-20B.

THE MICROORGANISM

*Micromonospora purpurea* JI-20 is very similar in taxonomical and morphological properties to *M. purpurea* NRRL 2953 which are described in U.S. Pat. No. 3,091,572 issued May 28, 1963. In fact few significant different in such properties have been noted. However, despite the fact that the mutant strain is quite similar to *M. purpurea* NRRL 2953 it has two distinguishing strain characteristics; one that it produces an antibiotic complex which differs substantially from that of the parent. Secondly, unlike *M. purpurea*, which usually produces a purple pigment, the mutant strain may produce diffusible pigments of various colors and shades, such as, red, pink, yellow, brown and gray-green. A typical strain of *Micromonospora purpurea* JI-20 has been deposited at the Northern Utilization Research and Development Division, U.S. Department of Agriculture, Peoria, Ill. where it was given the accession number NRRL 5467.

The mutant strain *Micromonospora purpurea* JI-20 was initially produced by the treatment of *Micromonospora purpurea* NRRL 2953 with nitrosoquanidine followed by strain selection. It is apparent that to those skilled in the art that other mutagenic agents and other standard techniques may be used to obtain microorganisms that are the equivalent of *M. purpurea* JI-20.

Table I sets forth the morphological properties of *Micromonospora purpurea* JI-20 and subsequent tables set forth additional data which enable taxonomic placement of the microorganism. In describing the color formation the following system and reference are employed: The color designation consists of two designates. The first is a color name taken from the "Descriptive Color Name Dictionary", by Taylor, Knoche and Granville, published by the Container Corporation of America, 1950 (U.S.A.), with a color chip number corresponding to the color name; said chip number taken from the "Color Harmony Manual", 4th edition, 1958, published by the Container Corporation of America, U.S.A. The second designate consists of a color-name and number which refers to the synonym or near synonym found in the National Bureau of Standards, Circular 553, November, 1955 (U.S.A.). The reverse color description utilize the same system of designates and are made by simply observing the culture through the bottom (reverse) of the petri dish.

TABLE I

Morphology of Micromonospora purpurea JI-20
Medium: 3% NZ Amine Type A, 1% Dextrose, 1.5% Agar
Observations

| Macroscopic | Microscopic |
| --- | --- |
| Growth moderate, plicate, no diffusible pigment, no aerial mycelium. Color g41c dusty orange, moderate orange 53 | Spores not observed on any of the media. Mycelium not fragmenting in young cultures but may undergo lysis in old cultures. Mycelium 0.4 – 0.6 μm in diameter. |

TABLE II

Colony Descriptions of Micromonospora purpurea JI-20 on Various Media

| Media | Observations |
| --- | --- |
| Glucose Asparagine Agar | Growth moderate, plicate, no aerial mycelium, no diffusible pigment, color: surface:g5pe terracotta; strong brown 55. Reverse g5pg henna; strong brown 55. |
| Milk | Growth good, plicate, no diffusible pigment, no aerial mycelium, hydrolysis positive (+++); surface color: g3ic light amber; dark orange yellow 72 |
| Sucrose | Growth good, plicate, dark maroon |
| Starch | Growth good, plicate, dark maroon |
| Cellulose | Growth fair, cellulose undergoing decomposition |
| Bennett's Agar | Growth good, plicate, no diffusible pigment, no aerial mycelium; color: surface center: g4gc nude, tan; light brown 57. Periphery: g51g cocoa brown; moderate reddish brown 43. Reverse m4pg dark luggage tan, strong brown 55. |
| Emerson's Agar | Growth moderate, plicate-membranous, no diffusible pigment, no aerial mycelium, color: surface: g51e rust tan; grayish reddish orange 39. Reverse g4nc luggage tan; strong brown 55. |
| Tomato Paste Oatmeal Agar | Growth good, plicate - membranous no diffusible pigment, no aerial mycelium; color; surface g41a orange; strong orange 50. Reverse not detectable |
| Glucose Asparagine Agar | Growth moderate, plicate - membranous, no diffusible pigment, no aerial mycelium, color: surface g5pe terra cotta; strong brown 55. Reverse m5pe terra cotta, brownish orange 54. |
| Glucose Yeast Extract Agar | Growth good, plicate - membranous, no diffusible pigment, no aerial mycelium, color: surface g3gc light tan, light yellowish brown 76. Reverse m31e cinnamon; light yellowish brown 76. |
| Potato | +CaCO₃ ∓ CaCO₃ +++ (Growth good) - (Growth poor) g8pe (periphery) burgundy: dark reddish brown 44 g5ic (center) light persimmon; moderate reddish orange 37. |
| Sucrose | Growth moderate, plicate, no |

TABLE II-continued

Colony Descriptions of Micromonospora purpurea JI-20 on Various Media

| Media | Observations |
|---|---|
| Nitrate Agar (Czapek's Agar) | diffusible pigment, no aerial mycelium, color: surface g10pn dark egg plant; blackish purple 250. Reverse m8pn ebony brown; dark reddish gray 23. |
| Tyrosine Agar Observations at 2, 7, and 14 days (after Gordon and Smith J. Bact. 69:147) | Growth poor, slight brown diffusible pigment |
| Peptone Iron Agar Observations at 2, 7, and 14 days | Growth poor, no reaction |
| Litmus Milk | Milk completely peptonized, acid reaction |

TABLE III

Utilization of Nitrogen Sources by Micromonospora purpurea JI-20

| Nitrogen Source +1% glucose | |
|---|---|
| 0.5% Difco Yeast Extract | Growth moderate, membranous to plicate, no diffusible pigment, no aerial mycelium, color: surface g7-1/21 g rose mauve; dark grayish purple 229. Reverse m6pi brown mahogany; moderate reddish brown 43. |
| 1.0% NZ Amine Type A | Growth moderate, membranous, no diffusible pigment, no aerial mycelium, color surface: g10ni egg plant; dark reddish purple 242. Reverse m6pi brown mahogany; moderate reddish brown 43. |
| 1% Asparagine | Growth poor, flat, no diffusible pigment, no aerial mycelium, surface color g7-1/2pi, dark wine; dark reddish brown 44. Reverse m7-1/2pi dark wine; dark red 16. |
| 1% Glutamic Acid | Growth poor, flat, no diffusible pigment, no aerial mycelium, color: surface g7pl burgundy; dark grayish reddish brown 47. Reverse m6pl deep brown mahogany; grayish reddish brown 46. |
| 1% Sodium Nitrate | Growth poor |
| 1% Ammonium Nitrate | Growth poor |

| Sodium Chloride Tolerance | | | | | | |
|---|---|---|---|---|---|---|
| 0% | 1.5% | 3.0% | 4.0% | 5.0% | 7.0% | |
| +++ | +++ | +++ | ± | ± | ± | 12 days |

The microorganism generally tolerates up to 3% sodium chloride. Further, the microorganism grows well at temperatures between 25° and 38° C, grows poorly above 38° C and exhibits substantially no growth at 45° C or above.

The microorganism is variable with respect to nitrate reduction giving a positive reaction sometimes and a negative reaction at other times. The variability may be associated with the vigor with which the culture is growing at the time the test is performed.

The carbohydrate utilization pattern of Micromonospora JI-20 is substantially as follows:

The microorganism exhibits good growth on sucrose, xylose and mannose. Its growth on L-arabinose, glucose, lactose, starch and ribose is moderate. On cellulose, galactose, levulose raffinose, rhamnose, inositol, mannitol, sorbitol, glycerol, melizitose, D-arabinose, salicin and α-melibiose, the microorganism growth ranges from fair to poor. The control medium in which the growth tests were effected consists of 0.5% yeast extract without added carbohydrate upon which medium growth is poor. Thus, any improvement in the growth characteristics of the microorganism is due to the utilization of the carbohydrate.

The Fermentation

The fermentation of *Micromonospora purpurea* JI-20 to produce an antibiotic complex is usually effected in two and sometimes in three stages (i.e. germination and production). The first stage or the first two stages are devoted to germination of the microorganism to produce a suitable inoculum and is usually effected at temperatures within the range of from about 25° to about 35° C for 1 to 4 days. Further, the germination stage is effected under aerobic conditions with agitation, preferably rotary agitation. The production stage is commenced by inoculating, under sterile conditions, a suitable medium with the previously prepared inoculum. This stage of the fermentation is usually effected at about the same temperature range as the germination stage and usually requires from about 4 to about 7 days. However, unlike the germination stage where the pH usually remains fairly stable, the production stage requires regulation of the pH to keep it within the preferred range of from about 6.7 to about 8.3. It is also usually necessary during the course of the fermentation to add suitable agents to minimize foaming. Such agents are widely known in the art and are commercially available. For example, a very suitable agent is GE-60, a silicone type antifoam agent which is a trademarked product of General Electric. During the course of the fermentation, and particularly after the first 24 hours, samples of the whole broth are taken for assay, (such as the one described below) to determined when peak antibiotic production is reached. When peak production is attained the antibiotics are isolated by the methods generally used for basic antibiotics. Exemplary of such methods are ion exchange resin extraction utilizing such cationic resins as IRC-50 (Rohm and Haas, Philadelphia, Pa.), Lewatit CNP (Farben Fabriken Bayer, Leverkusen Germany), or the like. Further methods of isolation include solvent extraction of a suitable derivative (e.g. a Schiff base), adsorption on activated carbon or the like.

The Assay

Peak antibiotic production is determined by a discplate assay which uses *Staphylococcus aureus* ATCC 6538P as the test organism and which is performed substantially as described by Oden, et al. Antimicrobial Agents and Chemotherapy, 1963, pages 8–13.

The reference standard is Antibiotic JI-20B base having an assigned potency of 1000 mcg/mg. One (1) microgram of the standard in one (1) ml. of 0.1M phosphate buffer at pH 8.0 elicits a zonal response of 16.8± 1.5 mm. The standard Antibiotic JI-20B sulfate assays 730 mcg/mg against the standard base. Antibiotic JI-20A base and the corresponding sulfate assay 723 mcg/mg. and 527 mcg/mg., respectively, when assayed against the standard Antibiotic JI-20B base.

The Antibiotic

As previously stated the product elaborated by Micromonospora JI-20 is an antibiotic complex. When separated by a chromatographic method described hereinafter, gentamicin (i.e. gentamicin $C_1$, $C_2$ and $C_{1a}$) is the first to emerge. It is followed by Antibiotic JI-20B which is usually the most abundantly produced compound. The last compound to emerge is Antibiotic JI-20A.

The structure, physicochemical and biological properties of the components of gentamicin are well known having been reported in the Journal of Infectious Diseases Vol. 119, numbers 4 and 5, University of Chicago Press.

The physicochemical properties of the components of the Antibiotic JI-20A and Antibiotic JI-20B are substantially as set forth below:

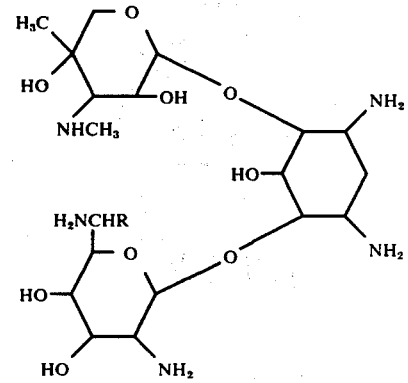

I wherein R is a member selected from the group consisting of hydrogen and methyl. In Antibiotic JI-20B, R is methyl. In Antibiotic JI-20A, R is hydrogen.

|  | Antibiotic JI-20A | Antibiotic JI-20 |
|---|---|---|
| Optical Rotation (water)$[\alpha]_D^{26}$ C=0.3% | +160° | +172° |
| pKa | 8.1 | 8.1 |
| Microanalysis Found |  |  |
| Carbon | 45.66% | 46.47% |
| Hydrogen | 8.18% | 8.45% |
| Nitrogen | 13.53% | 13.93% |
| Calculated Empirical Formula | $C_{19}H_{39}N_5O_9 \cdot H_2O$ | $C_{20}H_{41}N_5O_9 \cdot H_2O$ |
| N.M.R. Spectrum | FIG. 1 | FIG. 2 |
| Sulfate Salt |  |  |
|  | JI-20A | JI-20B |
| Carbon | 30.64 | 30.73 |
| Hydrogen | 6.55 | 6.70 |
| Nitrogen | 8.78 | 8.71 |
| N.M.R. Spectrum | As shown in FIG. 3 | As shown in FIG. 4 |
| Calculated Empirical Formula | $C_{19}H_{39}N_5O_9 \cdot 2½ H_2SO_4 \cdot ½H_2O$ | $C_{20}H_{41}N_5O_9 \cdot 2½ H_2SO_4 \cdot 2H_2O$ |

Antibiotic JI-20 complex, the novel components thereof (i.e. Antibiotic JI-20A and Antibiotic JI20B), and their acid addition salts form hydrates with water and solvates with polar organic solvents (e.g. alcoholates). These hydrates and solvates are the full biological equivalent of the basic antibiotic and their acid addition salts. They merely represent a form in which the antibiotics may be facilely recovered from solution.

Antibiotics JI-20A and JI-20B have characteristic nuclear magnetic resonance spectra as are shown in FIGS. 1 and 2, and their sulfates in FIGS. 3 and 4, respectively. These N.M.R. spectra were obtained by the use of a Varian A-60-A spectrometer (Varian Associates, 611 Hansen Way, Palo Alto, Calif.) on a solution of the antibiotic in deuterated water. The spectra are recorded in parts per million (PPM) using the HDO band at 4.61 PPM as the internal standard.

The components of the Antibiotic JI-20 complex have the gross (flat) structures depicted by Formula I. However, no conclusions relative to stereochemistry are to be drawn from the formula:

The compounds of this invention (i.e. Antibiotic JI-20A and Antibiotic JI-20B) may also be depicted stereochemically as set forth in Formulae Ia and Ib, respectively,

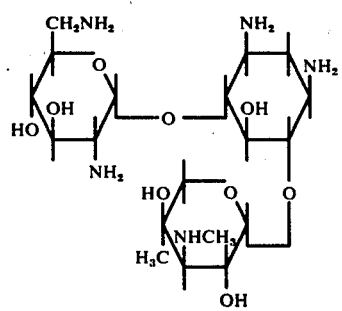

Ia

-continued

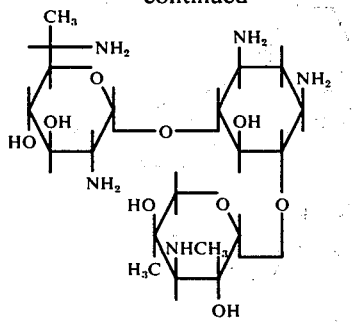

Ib

As can be seen by Formulae Ia and Ib, Antibiotic JI-20A and Antibiotic JI-20B are aminoglycoside antibiotics, which belong to the class that includes gentamicin, streptomycin, neomycin, paromomycin, sisomicin, kanamycin, and the like. The members of this class are basic antibiotics and are capable of being converted to certain non-toxic pharmaceutically acceptable derivatives having substantially the same antibiotic utility as the antibiotic free base, usually differing only in degree. Among such derivatives are acid addition salts and Schiff base-oxazolidine derivatives.

The pharmaceutically acceptable acid addition salts of Antibiotic JI-20A and Antibiotic JI-20B are generally prepared by titrating the free nitrogen base with acid. The salt is, advantageously, isolated by precipitation from an aqueous solution by a water miscible organic solvent, preferably a lower alcohol or by lyophilizing an aqueous solution of said salt. Such salts are generally derived from inorganic acids, such as the mineral acids and from hydrocarbon carboxylic acids such as the aliphatic acids including straight chain, branched chain and cyclic aliphatic acids; aromatic hydrocarbon carboxylic acids and aralkyl hydrocarbon carboxylic acids. Exemplary of such acids are sulfuric, hydrochloric, phosphoric, cyclopropanecarboxylic, adamantane carboxylic, benzoic, pivalic, phenylacetic, acetic, propionic, caproic, stearic and oleic acids.

Similarly, the pharmaceutically acceptable Schiff base-oxazolidine derivatives of Antibiotic JI-20A and Antibiotic JI-20B are generally prepared by treating an alcoholic solution of the antibiotic base with an excess of aldehyde at or above ambient temperature for about 1 hour, chilling the solution to obtain the desired product, usually in the form of a crystalline solid. Alternatively, these derivatives may be isolated by precipitation from a concentrate of the reaction mixture. As can be seen from Formula I, the antibiotic has four primary amino groups, each of which can form a Schiff base. Further, the antibiotic has a secondary amino group vicinal to a tertiary hydroxy group, which on combination with an aldehyde given rise to an oxazolidine ring. Thus when the antibiotic is reacted with an excess of aldehyde, five moles of aldehyde react with each mole of antibiotic to yeild the Schiff base-oxazolidine derivative depicted by formula II.

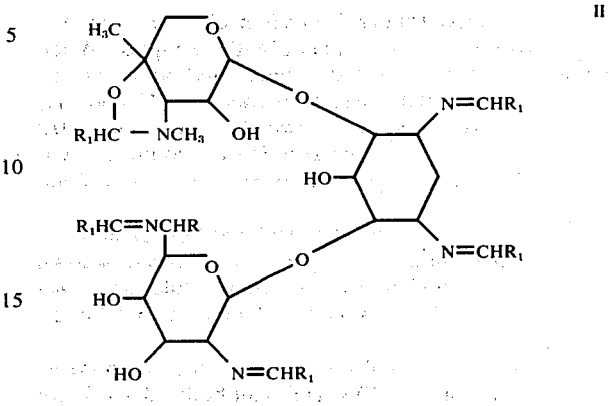

II wherein R is a member selected from the group consisting of hydrogen and methyl; $R_1HC=$ is an alkylidene radical containing 2 to 12 carbon atoms; a cycloalkylidene radical containing 4 to 12 carbon atoms; and aralkylidene radical containing 7 to 12 carbon atoms; or an heterocyclic radical containing 6 to 12 carbon atoms.

Representative of various aldehydes which upon reaction with the Antibiotic JI-20 complex and the components thereof so as to provide a derivative of formula II are: acetaldehyde, propionaldehyde, butyraldehyde, crotonaldehyde, furfural, cyclopentylacetaldehyde, vanillin, veratraldehyde, benzaldehyde, p-nitro-benzaldehyde, salicylaldehyde, pyridoxal and the like.

These Schiff base-oxazolidine derivatives are not appreciably soluble in water but are soluble in most commonly used organic solvents such as chloroform, methanol, acetone, ethyl acetate and the like. Further, the Schiff-base-oxazolidine derivatives are usually unstable in organic solvent containing traces of water and tend to revert to the free antibiotic. The presence of a trace amount of acid facilitates the reversion.

Biological Activity of Antiobiotics JI-20B Complex, JI-20A and JI-20B

Antibiotic JI-20 complex exhibits substantial antibacterial activity when tested in vitro in Mueller-Hinton broth. The minimum inhibitory concentration against 32 strains of *Escherichia coli* ranged from 0.3 to 50 mcg/ml.

The individual components and therefore the complex, exhibit a broad spectrum of in vitro antibacterial activity. In the table set forth below are test results after 24 hours incubation against representative gram positive and gram negative bacteria. These data were also obtained from tests performed with Mueller-Hinton broth, the values being expressed in terms of the antibiotic free base although the tests are actually performed with the sulfate salt.

| | MIC (mcg/ml) | |
|---|---|---|
| Organism | Antibiotic JI-20A | Antibiotic JI-20B |
| Staphylococcus aureus 70 | 3.0 | 3.0 |
| Staphylococcus aureus 2059 | 7.5 | 7.5 |
| Staphylococcus aureus 45 | 0.3 | 0.3 |
| Escherichia coli 11775 | 0.3 | 0.8 |
| Escherichia coli 12740 | 0.3 | 0.3 |
| Klebsiella pneumoniae 18 | 7.5 | 17.5 |
| Klebsiella pneumonia 13883 | 7.05 | 0.08 |

-continued

| | MIC (mcg/ml) | |
|---|---|---|
| Organism | Antibiotic JI-20A | Antibiotic JI-20B |
| Klebsiella rhinoscleromatis 18804 | 0.05 | 0.08 |
| Proteus mirabilis 8019 | 0.8 | 0.8 |
| Pseudomonas aeruginosa 59 | 3.0 | 7.5 |
| Pseudomonas aeruginosa 60 | 3.0 | 17.5 |

Antibiotic JI-20A and Antibiotic JI-20B exhibit an antibacterial action against pathogenic bacterial infections induced in laboratory animals and in particular in the mouse. To determine the in vivo protective activity of the antibiotics against lethal infections of pathogenic bacterial origin in mice, mice were dosed twice with the individual antibiotic, with a solution or a suspension in an aqueous vehicle containing 0.5% carboxy-methyl-cellulose (CMC), once immediately before an intraperitoneal injection of the infecting bacteria and once 4 hours after such injection. The number of survivors was determined 48 hours after infection and that data analyzed by standard probit procedures to determine $PD_{50}$ values with 95% confidence limits. The following chart sets forth the protective activity of the antibiotics against a pathogenic bacterium.

| | Protection Tests | |
|---|---|---|
| In vivo (Mouse) | | $PD_{50}$ mg/kg |
| Infecting Organism | Antibiotic JI-20A | Antibiotic JI-20B |
| Staphylococcus aureus | 2.9 | 14.0 |
| Gray 979 | 3.0 | 2.8 |
| Streptococcus pyogenes C2V | 40.0 | 40.0 |
| Pseudomonas aeruginosa 413 | 50.0 | 50.0 |
| 1516-7 | 50.0 | 50.0 |
| Escherichia coli 626 | 15.0 | 15.0 |
| 11775 | 4.0 | 8.0 |
| Salmonella sp. S.C. | 3.0 | 4.5 |

| Acute Toxicity | |
|---|---|
| $LD_{50}$ (mg/kg) | |
| I.V. | 115 | 115 |

Antibiotic JI-20 complex or the novel components thereof (JI-20A or JI-20B) and their acid addition salts may be used alone or in combination with detergents and/or other antibacterial agents to prevent the growth of, or to reduce the number of susceptible organism especially those set forth hereinabove. Thus, the antibiotics may be used in wash solutions for sanitary purposes, as in the cleaning of laboratory glassware and equipment. Further, they may be used for laundering purposes, such as a bacteriostatic rinse for laboratory uniforms.

The total antibiotic complex consisting of gentamicin, Antibiotic JI-20A and Antibiotic JI-20B may also be utilized for the above-mentioned purposes. Thus, the necessary for separating the antibiotic mixture may be obviated.

The Schiff base-oxazolidine derivatives of the antibiotics are especially useful as bacteriostats in oils and greases such as oil-based paints, cutting oils, lubricating greases and the like.

Preparation of Stock Culture

Prepare and sterilize a series of 300 ml. shake flasks with a medium having the following composition: beef extract (0.3%), tryptone (0.5%), yeast extract (0.5%), soluble starch (2.4%), dextrose (0.1%), calcium carbonate (0.1%) and water 100 ml. (All percentages are expressed as weight to volume.) Inoculate each flask with colonies of Micromonospora purpurea JI-20 from a sterile needle or loop. Ferment the mixture for from about 48 to about 72 hours at about 28° C with rotary agitation.

Prepare and sterilize a series of 3 liter flasks containing 1 liter of the above-described medium and inoculate with 50-100 ml. of the fermentation mixture from above. Repeat the above-described fermentation, and under sterile conditions, pool the fermented media. Under sterile conditions, centrifuge the media, remove the supernatant and wash the sediment containing the cellular mycelium with sterile water. The cellular mycelium and residual water is kept at sub-zero temperatures as a stock culture.

The following examples will illustrate the invention described herein without unduly restricting it.

EXAMPLE 1

Production of Gentamicin and Antibiotic JI-20 Complex

A. Inoculum Preparation

Prepare and sterilize a nutrient medium consisting of the following materials: beef extract (3 gms); tryptone (5 gms); dextrose (1 gm.); soluble starch (24 gms); yeast extract (5 gms); calcium carbonate (1 gm.) and water 1 liter in a 3 liter shake flask. Cool the sterile medium to about 25° C and inoculate with 5% (v/v) of a previously prepared stock culture of Micromonospora purpurea JI-20. Allow the culture to grow for from about 48 to about 72 hours at 28° C with rotary agitation at about 280 rpm.

B. Second Inoculum

Using a 10 liter aerated and agitated fermentor, prepare and sterilize the following medium: Soybean meal (210 gms.); dextrin (300 gms.); cerelose (30 gms.); calcium carbonate (42 gms); cobalt chloride (12 mgms); GE-60 antifoam (3 ml.) and water to 6 liters.

Transfer under aseptic conditions, 600 ml. of the inoculum from step A to the sterile medium prepared in this step. Ferment the mixture at about 34° C with aeration at about 5 liters/minute, agitation at about 500 rpm until a "packed cell volume" of at least 15–20% is attained (22–26 hours).

C. Antibiotic Production Stage

Prepare and sterilize 90 liters of fermentation medium containing the following nutrients: Soybean meal (3.15 kg); dextrin (4.5 kg.); cerelose (450 gm.); cobalt chloride (200 mg.); calcium carbonate (630 gms.); GE-60 antifoam (100 ml.) and water to 90 liters. Adjust the post sterilization pH to 7.3 with dilute acid or alkali as required. Cool the medium to about 34° C and, under sterile conditions, add 6 liters of inoculum prepared in step B. Ferment the mixture at 34° C with aeration at about 1.2 cu. ft./minute, agitation at from about 200 to about 400 rpm. and at a pH ranging from about 6.7 to about 8.3. Assay the fermentation after 24 hours, again after 48 hours and at 12 hour intervals thereafter until peak production is reached. Isolate the products by the procedure described in Example 2.

EXAMPLE 2

Isolation of the Antibiotic Mixture

Add 630 gms. of oxalic acid to the fermentation medium with agitation and adjust the mixture to pH 2 using 6N sulfuric acid. Agitate the mixture for about 20 minutes and filter. Wash the mycelial cake with water and combine the washing and the filtered broth. Neutralize the combined filtrate and washes with 6N ammonium hydroxide. Adsorb the antibiotic complex on IRC-50 resin in the ammonium form by passing the neutral broth through a column of resin which is about 2 inches in diameter and about 26 inches in height. Wash the resin bed with deionized water until the residual broth is removed (washes are free of color), elute the column with 2N ammonium hydroxide until the effluent is strongly basic (e.g. pH 10 or above) and wash with deionized water.

Pass the eluate and washes through a previously prepared column of IRA-401S resin (hydroxyl cycle) to decolorize, the column having at least the dimensions described above for the IRC-50 column. The effluent and washes from the IRA-401S column are combined and concentrated in vacuo to about 4.3 liters. Lyophilize 100 ml. of the concentrate to obtain 1.6 gms. of Antibiotic JI-20 complex assaying 591 mcg/mg. (vs. *S. aureus*, gentamicin = 1000).

EXAMPLE 3

Separation of the Antibiotic Mixture

Chromatograph 1.5 gms. of the antibiotic mixture obtained in Example 2, on a column of silica gel. As the eluent, use the lower phase of a 1:1:1 chloroform-methanol concentrated ammonium hydroxide system. Monitor the column by taking a sample of each fraction collected, subjecting it to thin-layer chromatography on silica gel plates followed by bioautography against *Staphylococcus aureus* ATCC 6538P. Combine the eluate fractions containing each antibiotic, concentrate the eluate in vacuo to about 50–100 ml. and lyophilize to obtain, in the order of their emergence from the column, gentamicin, Antibiotic JI-20B and Antibiotic JI-20A.

EXAMPLE 4

Preparation of Antibiotic JI-20 Complex Sulfate

Dissolve 7.5 g. of Antibiotic JI-20 complex as prepared in Example 2 in 60 ml. of water and adjust the pH to about 4.0 by the addition of 12N sulfuric acid. Add decolorizing charcoal and stir for 30 minutes. Filter the solution and pour into 650 ml. of methanol. Collect the product by filtration, wash with methanol and dry under reduced pressure at about 55° C to obtain the product of this example, $[\alpha]_D^{26} = +119°$ (water), bioassay 516 mcg/mg.

EXAMPLE 5

Preparation of Antibiotic JI-20 Complex Hydrochloride

Dissolve 2.0 g. of JI-20 complex in 15 ml. of water and add 6N hydrochloric acid dropwise with stirring to pH 3.6. Add decolorizing charcoal and stir for 15 minutes. Filter the solution and pour the filtrate into 500 ml. of acetone. Decant the supernatant liquid from the resulting precipitated gum. Dissolve the residual gum in water and lyophilize to obtain the desired material, m.p. 208°–213° dec., $[\alpha]_D^{26} = +128°$ (water).

EXAMPLE 6

Preparation of Antibiotic JI-20B Sulfate

Dissolve 3 g. of JI-20B in 24 ml. of water and adjust the pH to about 4.0 by the addition of 6N sulfuric acid. Add decolorizing charcoal and stir for 30 minutes. Filter the solution and pour into 250 ml. of methanol. Filter off the precipitated product, wash with methanol and dry under reduced pressure to obtain the desired sulfate salt, $[\alpha]_D^{26} = +120°$ (water), bioassay 758 mcg/mg.

EXAMPLE 7

Preparation of Antibiotic JI-20A Sulfate

According to the procedure of example 6, add sulfuric acid to an aqueous solution of 1.5 g. of JI-20A and isolate the desired sulfate as described, $[\alpha]_D^{26} = +115°$ (water), bioassay 458 mcg/mg.

EXAMPLE 8

Salicylaldehyde Schiff Base-Oxazolidine Derivative of Antibiotic JI-20B

Stir 250 mg. of JI-20B in 10 ml. of anhydrous ethanol and add 0.4 ml. of salicylaldehyde. Stir for about 48 hours, then concentrate the reaction mixture to about 5 ml. under reduced pressure and pour into 100 ml. of water. Isolate the precipitate by filtration, wash with water and dry under reduced pressure to obtain the title compound, m.p. 186°–190°, $[\alpha]_D^{26} = +161°$ (ethanol).

EXAMPLE 9

Benzaldehyde Schiff Base-Oxazolidine Derivative of Antibiotic JI-20B

Stir 250 mg. of JI-20B in 10 ml. of anhydrous ethanol and add 0.4 ml. of benzaldehyde. Stir for about 48 hours, then concentrate to a small volume under reduced pressure and pour into a mixture of ether and hexane. Isolate the resulting precipitate by filtration, wash with hexane and dry under reduced pressure to obtain the title compound, m.p. 155°–158°, $[\alpha]_D^{26} = +69°$ (ethanol).

EXAMPLE 10 p-Chlorobenzaldehyde Schiff Base-Oxazolidine Derivative of Antibiotic JI-20B Stir 250 mg. of JI-20B in 10 ml. of anhydrous ethanol and add 425 mg. of p-chlorobenzaldehyde. Stir for 24 hours, concentrate to about 2 ml. under reduced pressure, dilute with 2 ml. of methanol and pour into 50 ml. of stirred water. Isolate the resulting precipitate by filtration, wash with water and dry under reduced pressure to obtain the title compound, m.p. 161°–165°, $[\alpha]_D^{26} = +147°$ (ethanol).

EXAMPLE 11

Propionaldehyde Schiff Base-Oxazolidine Derivative of Antibiotic JI-20B

Heat 1.0 g. of JI-20B in 20 ml. of anhydrous ethanol to about 75° and add 0.9 ml. of propionaldehyde. Heat the mixture at about 75° for 18 hours, then concentrate to about 4 ml. under reduced pressure. Add the concentrated solution dropwise to 200 ml of stirred ether and isolate the resulting precipitate by filtration. Wash the precipitate with ether and dry to obtain the compound of this example, m.p. 163-168°, $[\alpha]_D^{26} = +68°$ (ethanol).

By replacing Antibiotic JI-20B in examples 8 through 11 inclusive with an equivalent quantity of Antibiotic JI-20A or Antibiotic JI-20 complex and by following the process of the respective examples, the corresponding Schiff base-oxazolidine derivatives of Antibiotic JI-20A or of Antibiotic JI-20 complex may be prepared.

Antibiotic JI-20 complex, the components thereof and/or the above-described acid addition salts or Schiff base-oxazolidine derivatives thereof may be administered orally. They may also be applied topically in the form of ointments, both hydrophilic and hydrophobic, in the form of lotions which may be aqueous, non-aqueous or of the emulsion type or in the form of creams. Pharmaceutical carriers useful in the preparation of such formulations will include, for example, such substances as water, oils, greases, polyesters, polyols and the like. The Schiff base-oxazolidine derivatives are of particular advantage for preparing non-aqueous topical formulations since such derivatives exhibit compatibility with the pharmaceutical carriers generally used in such preparations.

When administered orally the antibiotics of this invention may be compounded in the form of tablets, capsules, elixirs or the like or may even be admixed with animal feed. It is in these dosage forms that the antibiotics are most effective for treating bacterial infections of the gastrointestinal tract, which infections cause non-specific diarrheas. When the animal species are being treated orally, the antibiotics of this invention are administered at from about 5 mg. to about 50 mg. per kilogram of body weight per day, preferably divided into from about 2 to about 4 doses.

In general, the topical preparations will contain from about 0.1 to about 3.0 gms. of antibiotic per 100 gms. of ointment, cream or lotion. The topical preparations are usually applied gently to lesions from about 2 to about 5 times a day.

The antibiotics of this invention may be utilized in liquid form such as solutions, suspensions and the like for otic and optic use and may also be administered parenterally via intramuscular injection. The injectable solution or suspension will usually be administered at from about 2 mg. to about 15 mgs. of antibiotic per kilogram of body weight per day divided into about 2 to about 4 doses. The precise dose depends on the stage and severity of the infection, the susceptibility of the infecting organism to the antibiotic and the individual characteristics of the animal species being treated.

The following examples are to exemplify some of the dosage forms in which the antibiotics of this invention and their derivatives may be employed:

EXAMPLE 12

| Tablet | 10 mg. Tab.* | 25 mg. Tab.* | 100 mg. Tab.* |
| --- | --- | --- | --- |
| Antibiotic JI-20 complex | 10.50 mg. | 26.25 mg. | 105.00 mg. |
| Lactose, impalpable powder | 197.50 mg. | 171.25 mg. | 126.00 mg. |
| Corn starch | 25.00 mg. | 25.00 mg. | 35.00 mg. |
| Polyvinylpyrrolidone | 7.50 mg. | 7.50 mg. | 7.50 mg. |
| Magnesium Stearate | 2.50 mg. | 2.50 mg. | 3.50 mg. |

*5% excess

Procedure

Prepare a slurry consisting of the Antibiotic JI-20 complex, lactose and polyvinylpyrrolidone. Spray dry the slurry. Add the corn starch and magnesium stearate. Mix and compress into tablets.

EXAMPLE 13

| Bolus | 100 mg. Bolus* |
| --- | --- |
| Antibiotic JI-20B (sulfate) | 105.00 mg. |
| Lactose | 4600.00 mg. |
| Corn Starch (pregelatinized) | 1100 mg. |
| Magnesium Stearate | 95.00 mg. |
| Water | 100.00 ml. |
| | 6000.00 |

*5% excess

Procedure

Mix the Antibiotic JI-20B (sulfate), lactose and a portion of the corn starch in a suitable mixing bowl. Prepare a paste of a portion of the corn starch and the water and use this paste to prepare a damp mass of the above powders. Screen the mass to produce granules. Dry the granules. Reduce the dried granules to a specific particle size. Add the magnesium stearate, mix and compress the granulation into tablets (bolus) using suitable equipment.

EXAMPLE 14

| Ointment | |
| --- | --- |
| Antibiotic JI-20A (Base) | 1.0 gm. |
| Methyl paraben U.S.P. | 0.5 gm. |
| Propyl paraben U.S.P. | 0.1 gm. |
| Petrolatum | to 1000 gm. |

Procedure

1. Melt the petrolatum.
2. Mix the Antibiotic JI-20A, methyl paraben and propyl paraben with about 10% of the molten petrolatum.
3. Pass the mixture through a colloid mill.
4. Add the remainder of the petrolatum with agitation and cool the mixture until it becomes semi-solid. At this stage the product may be put into suitable containers.

Ointments of Antibiotic JI-20B, Antibiotic JI-20 complex or Schiff base-oxazolidine derivatives of such antibiotics or acid addition salts thereof may be prepared by substituting an equivalent quantity of antibiotic, derivative or acid addition salt for Antibiotic JI-20A in the foregoing example and by following substantially the procedure of the example.

EXAMPLE 15

| Injectable Solution | Per 2.0 ml. vial* | Per 50 Liters* |
| --- | --- | --- |
| Antibiotic JI-20B sulfate | 84.0 mgs. | 2100.0 gms. |
| Methyl paraben, U.S.P. | 3.6 mgs. | 90.0 gms. |
| Propyl paraben, U.S.P. | 0.4 mgs. | 10.0 gms. |
| Sodium bisulfate U.S.P. | 6.4 mgs. | 160.0 gms. |
| Disodium Ethylenediamine tetraacetate dihydrate, R.G. | 0.2 mgs. | 5.0 gms. |
| Water, U.S.P. q.s. | 2.0 ml. | 50.0 liter |

*Includes a 5% manufacturing overcharge.

Procedure: For a 50.0 liter batch

Charge approximately 35 liters of water for injection to a suitable stainless steel jacketed vessel and heat to about 70° C. Charge the methylparaben and propylparaben to the heated water for injection and dissolve with agitation. When the parabens are completely dissolved, cool the contents of the tank to 25–30° C by circulating cold water through the tank jacket. Sparge the solution with nitrogen gas for at least 10 minutes and keep covered with nitrogen during subsequent processing. Charge and dissolve the disodium EDTA and sodium bisulfite. Charge and dissolve the Antibiotic JI-20B sulfate. Bring the batch volume up to 50.0 liters with water for injection and agitate until homogenous.

Under sterile conditions, filter the solution through a suitable bacteria retentive filter collecting the filtrate in a filling tank.

Fill the filtrate aseptically into sterile pyrogen free multiple dose vials, stopper and seal.

In like manner, injectable solutions of Antibiotic JI-20A, Antibiotic JI-20 complex and especially acid addition salts of such antibiotics may be prepared by substituting an equivalent quantity of such compounds for Antibiotic JI-20B sulfate and by following the procedure set forth above.

We claim:

1. A composition having antibiotic activity, said composition consisting essentially of a mixture of gentamicin, Antibiotic JI-20A and Antibiotic JI-20B.

2. A composition having antibiotic activity, said composition consisting essentially of an acid addition salt of gentamicin, Antibiotic JI-20A and Antibiotic JI-20B.

3. A method of eliciting an antibacterial response in animals having a bacterial infection which comprises administering a therapeutically effective quantity of a member selected from the group consisting of Antibiotic JI-20 complex, Antibiotic JI-20A, and Antibiotic JI-20B, or a pharmaceutically acceptable acid addition salt thereof or a Schiff-base oxazolidine derivative thereof in combination with a pharmaceutical carrier.

4. A method according to claim 3 wherein the antibacterial response is effected by topical application.

5. A method according to claim 3 wherein the antibacterial response is effected by parenteral administration.

6. A method according to claim 3 wherein the antibacterial response is effected by oral administration.

* * * * *